US00PP12708P2

(12) United States Plant Patent
Westhoff

(10) Patent No.: US PP12,708 P2
(45) Date of Patent: Jun. 18, 2002

(54) LOBELIA PLANT NAMED 'WESLOWEI'

(75) Inventor: Heinrich Westhoff, Sudlohn-Oeding (DE)

(73) Assignee: Josef & Heinrich Westhoff Gartenbau-Spezialkulturen, Sudlohn-Oeding (DE)

( * ) Notice: Subject to any disclaimer, the term of this patent is extended or adjusted under 35 U.S.C. 154(b) by 4 days.

(21) Appl. No.: 09/728,983

(22) Filed: Dec. 4, 2000

(51) Int. Cl.[7] ..... A01H 5/00
(52) U.S. Cl. ..... Plt./263
(58) Field of Search ..... Plt./263

(56) References Cited

PUBLICATIONS

GTITM UPOVROM Citation for 'Weslowei' as per QZ PBR 980742; May 29, 1998.*

* cited by examiner

*Primary Examiner*—Bruce R. Campell
*Assistant Examiner*—Kent L. Bell
(74) *Attorney, Agent, or Firm*—C. A. Whealy

(57) ABSTRACT

A distinct cultivar of Lobelia plant named 'Weslowei', characterized by its cascading and rounded plant habit; short internodes, dense and bushy plant form; vigorous growth habit; dark green leaves; and pure white-colored flowers.

1 Drawing Sheet

BACKGROUND OF THE INVENTION

The present Invention relates to a new and distinct cultivar of Lobelia plant, botanically known as *Lobelia erinus L.*, and hereinafter referred to by the cultivar name 'Weslowei'.

The new Lobelia is a product of a planned breeding program conducted by the Inventor in Sudlohn-Oeding, Germany. The new Lobelia originated from a cross made by the Inventor of the Lobelia cultivar 'Wesstar', disclosed in U.S. Plant patent application Ser. No. 09/324,081, as the female, or seed, parent with an unnamed white Lobelia selection, not patented, as the male, or pollen, parent. The new Lobelia was selected by the Inventor in 1997 on the basis of its pure white flowers.

Asexual reproduction of the new cultivar by terminal cuttings taken at Sudlohn-Oeding, Germany, has shown that the unique features of this new Lobelia are stable and reproduced true to type in successive generations.

SUMMARY OF THE INVENTION

Plants of the cultivar 'Weslowei' have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Weslowei'. These characteristics in combination distinguish 'Weslowei' as a new and distinct cultivar:

1. Cascading and rounded plant habit.
2. Short internodes, dense and bushy plant form.
3. Vigorous growth habit.
4. Dark green leaves.
5. Pure white-colored flowers.

Compared to plants of the female parent, the cultivar 'Wesstar', plants of the new Lobelia have broader petals, longer peduncles and smaller sepals. In addition, plants of the new Lobelia and the cultivar 'Wesstar' differ in flower color.

Compared to plants of the male parent, the unnamed white Lobelia selection, plants of the new Lobelia are more pendulous in plant habit and have shorter internodes, darker green leaves and larger flowers.

Plants of the cultivar 'Weslowei' are most similar plants of the cultivar 'Azuro', disclosed in U.S. Plant Pat. No. 10,758. However in side-by-side comparisons conducted by the Inventor in Sudlohn-Oeding, Germany, plants of the cultivar 'Weslowei' and the cultivar 'Azuro' differ in the following characteristics:

1. Plants of the new Lobelia have stronger lateral branches than plants of the cultivars 'Azuro'.
2. Plants of the new Lobelia have shorter internodes than plants of the cultivar 'Azuro'.
3. Plants of the new Lobelia have larger leaves than plants of the cultivar 'Azuro'.
4. Plants of the new Lobelia have smaller sepals than plants of the cultivar 'Azuro'.
5. Plants of the new Lobelia have white-colored flowers whereas plants of the cultivar 'Azuro' have blue-colored flowers.

BRIEF DISCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new Lobelia.

The photograph at the top of the sheet comprises a side perspective view of typical flowering plants of 'Weslowei' grown in a hanging basket.

The photograph at the bottom of the sheet comprises a close-up view of a typical flower of 'Weslowei'.

DETAILED BOTANICAL DESCRIPTION

In the following description, color references are made to The Royal Horticultural Society Colour Chart except where general terms of ordinary dictionary significance are used. Plants were grown under conditions which closely approximate commercial production conditions during the spring in Sudlohn-Oeding, Germany. Plants used for this description were grown as one plant per 12-cm container or three plants per 25-cm hanging basket container and were about 20 weeks from planting.

Botanical classification: *Lobelia erinus L.* cultivar 'Weslowei'.

Parentage:

*Female parent.*—*Lobelia erinus L.* cultivar 'Wesstar', disclosed in U.S. Plant patent application Ser. No. 09/324,081.

*Male parent.*—Unnamed white selection of *Lobelia erinus L.,* not patented.

Propagation:

*Type cutting.*—Terminal vegetative cuttings.

*Time to initiate and develop roots.*—About two weeks at 18 to 20° C.

*Root description.*—Fine, fibrous, and well-branched.

Plant description:

*Form.*—Cascading and rounded flowering perennial plants with pure white-colored flowers. Lateral shoots outwardly spreading; plants uniform and eventually become spherical in plant shape and relatively compact. Freely branching with lateral branches forming at very node; dense and bushy. Appropriate for 12-cm containers and 25-cm hanging basket containers.

*Usage.*—Appropriate for hanging baskets, window boxes and patio containers.

*Crop time.*—About 10 weeks are required to produce finished flowering plants in 12-cm containers.

*Plant height* (*soil level to top of plant plane*).—About 12.5 cm.

*Plant length* (*soil level to lateral branches apices*).—About 40 cm.

*Plant diameter.*—About 20 cm.

*Vigor.*—Vigorous growth habit.

*Lateral branch description.*—Length: About 40 cm. Diameter: About 1.65 mm. Internode length: About 1.3 to 2.2 cm. Cross-section: Square. Texture: Smooth. Color: 146B.

*Foliage description.*—Leaves simple, alternate. Aspect: Slightly cupped. Texture: Smooth. Basal leaves: Length: About 4.5 cm. Width: About 2.5 cm. Shape: Elliptic to rhomboid. Apex: Rounded. Base: Attenuate. Margin: Crenate. Petiole length: About 7 mm. Mid-plant leaves: Length: About 5 cm. Width: About 2.3 cm. Shape: Oblanceolate to spatulate. Apex: Retuse. Base: Attenuate. Margin: Somewhat crenate. Petiole length: About 1 cm. Apical leaves: Length: About 3.6 cm. Width: About 1.2 cm. Shape: Linear. Apex: Rounded. Base: Attenuate. Margin: Entire. Petiole length: Petiole not observed. Color, all leaves: Young foliage, upper surface: 146B. Young foliage, lower surface: 147C. Mature foliage, upper surface: 147A; veins, 146C. Mature foliage, lower surface: 148B; veins, 146C.

Flower description:

*Flower type and habit.*—Flowers arranged singly at lateral apices. Flowers held outwardly. Flowers persistent. Older flowers are overgrown by new flowers and foliage. Freely and continuously flowering. Flowers not fragrant.

*Flower shape.*—Tubular with three larger lower petals and two upright petals.

*Natural flowering season.*—Spring until frost in the autumn.

*Flower longevity on the plant.*—Longevity of individual flowers is highly dependent on weather conditions. Typically three to 10 days.

*Flower size.*—Diameter: About 2.2 cm. Depth (height): About 1.9 cm. Tube length: About 8 mm. Throat diameter, distal end: About 5 mm. Tube diameter, proximal end: About 3 mm.

*Peduncle.*—Strength: Flexible and wiry, flowers held outwardly. Length: About 2.7 cm. Diameter: About 0.8 to 1 mm. Color: 147A.

*Flower buds.*—Length: About 1.3 cm. Diameter: About 4 mm. Shape: Oblong. Color (during development): 145B to 145D to 157C.

*Petals.*—Arrangement: Single whorl of five petals, fused; three larger lower petals and two smaller upper petals. Three lower petals: Shape: Elliptic. Length, above throat: About 1.2 cm. Width: About 8 mm. Two upper petals: Shape: Oblong. Length, above throat: About 7 mm. Width: About 2.3 mm. Upper and lower petals: Apex: Cuspidate. Margin: Entire. Texture: Smooth, satiny. Color: Petal, upper and lower surfaces, when opening: Lighter than 155D. Petal, upper and lower surfaces, opened flower: Lighter than 155D. Throat: White, 155D, background with two greenish yellow, close to 153B, basal stripes.

*Sepals.*—Arrangement: Single whorl of five sepals, star-shaped. Length: About 7 mm. Width: About 1.5 mm. Shape: Narrowly lanceolate to needle-like. Apex: Acute. Margin: Entire. Texture: Smooth. Color: Upper surface: 147A. Lower surface: 147B.

*Reproductive organs.*—Stamens: Quantity: About five, fused. Filament color: 192D. Anther length: About 2.4 mm. Anther diameter: About 1.2 mm. Anther color: 201A with short white pubescence. Pollen amount: Moderate. Pollen color: 3A. Pistils: Quantity: One. Pistil length: About 9 mm. Stigma shape: Two kidney-shaped parts, fused, rounded. Stigma color: 79A with pubescence. Style length: About 6.75 mm. Style color: 146A. Ovary color: 146C.

*Seed.*—Seed production has not been observed.

Disease resistance: Plants of the new Lobelia have not been noted to be resistant to pathogens common to Lobelia.

Weather tolerance: Plants of the new Lobelia have exhibited good tolerance to rain and wind.

It is claimed:

1. A new and distinct cultivar of Lobelia plant named 'Weslowei', as illustrated and described.

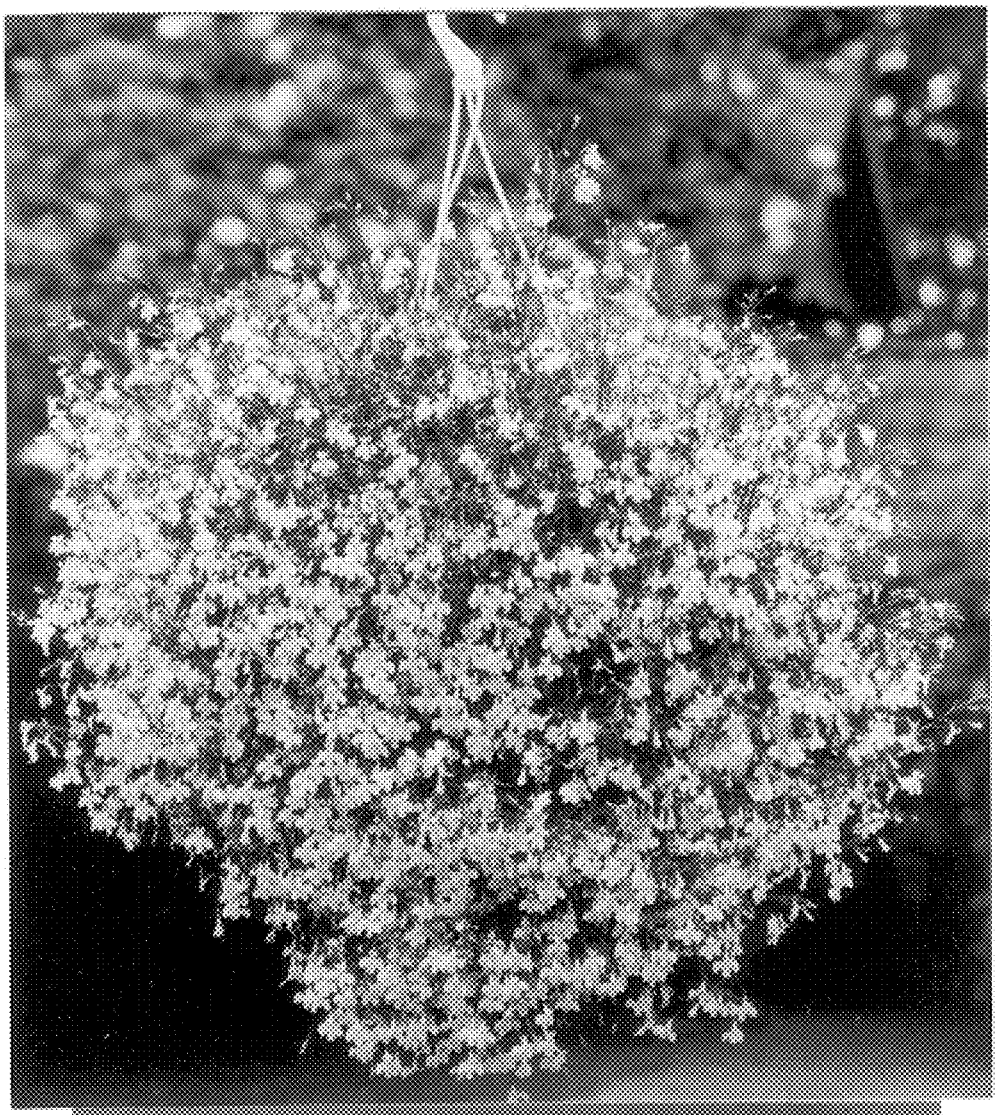
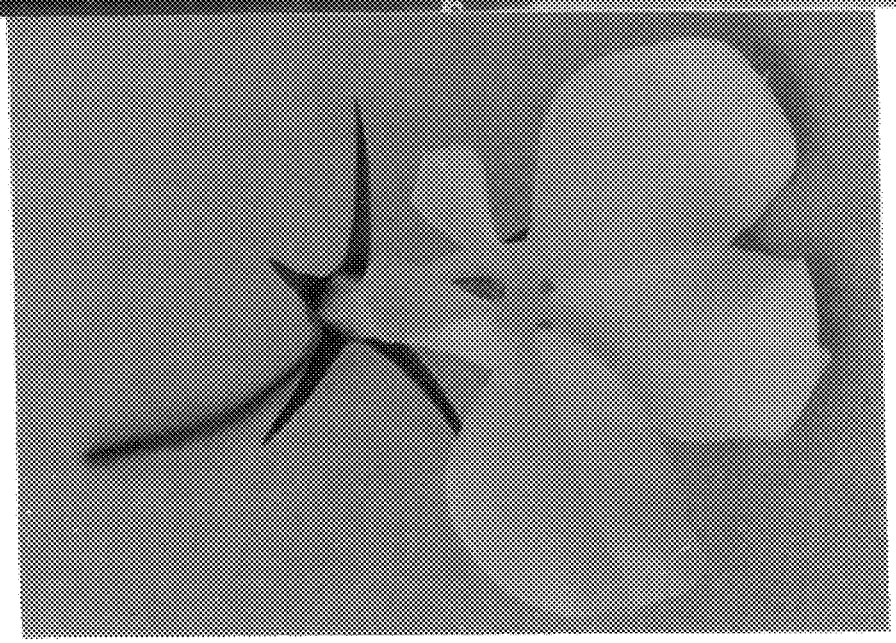

* * * * *